United States Patent [19]

Szepessy et al.

[11] Patent Number: 4,817,333

[45] Date of Patent: Apr. 4, 1989

[54] PROCESS FOR THE ACID-BASE DISINFECTION OF RICE SEEDS

[75] Inventors: István Szepessy; Ferenc Tundik, both of Debrecen; István Gyürk, Budapest; Ibolya S. née Kiss, Szarvas, all of Hungary

[73] Assignee: Debreceni Mezogazdasagi Gepgyarto Vallalat, Debrecen, Hungary

[21] Appl. No.: 53,153

[22] Filed: May 21, 1987

[30] Foreign Application Priority Data

May 21, 1986 [HU] Hungary ............................. 2154/86

[51] Int. Cl.[4] .......................... A01N 3/00; A01C 1/06; A01C 21/00
[52] U.S. Cl. .......................................... 47/58; 422/28; 47/57.6; 47/DIG. 9; 111/200
[58] Field of Search ..................... 422/28, 37; 426/331, 426/335, 629; 47/52.6, DIG. 9, 58; 111/1

[56] References Cited

U.S. PATENT DOCUMENTS

| 304,147 | 8/1884 | Taylor | 47/DIG. 9 |
| 1,718,332 | 12/1926 | Cloer | 47/DIG. 9 |
| 3,328,178 | 6/1967 | Alderton | 422/28 |

Primary Examiner—Barry S. Richman
Assistant Examiner—Lyle Alfandary-Alexander
Attorney, Agent, or Firm—Herbert Dubno; Jonathan Myers

[57] ABSTRACT

The present invention relates to a process for the disinfection of seeds, especially rice which comprises applying an acidic solution onto the surface of seeds, thereafter neutralizing the effect of the acid by the addition of an alkaline powder.

5 Claims, No Drawings

PROCESS FOR THE ACID-BASE DISINFECTION OF RICE SEEDS

TECHNICAL FIELD

The process of the invention relates to a new process for the acidic-basic disinfection, seed coating of seeds, especially rice.

BACKGROUND ART

It is well known in the art that the nematoda disease of rice is a wide-spread disease of rice and it causes the greatest losses of the crop (20–60%) in the countries situated in the temperate zone. (Hashioka, Y.: Nematoda Diseases of Rice in the World, 11 Riso, Milano, 1964; Economic Nematology, 1972, Academic Press, London-New York; Rice Diseases, Commonwealth Mycological Inst., Kew, Surrey, England, 1972).

the symptoms of the said disease were observed only at the end of the 1960, i.e. the discovery of the spreading of leaf nematoda causing the disease and the search for the processes suitable for avoiding said disease were started at that time in Hungary. (Jávor, I.: The Spreading of Rice Nematoda, Damage of the Same and the possibilities of Control, Növényvédelem, 1973, 9. 2.) The first great damage of the crop which could be attributed to nematoda was observed on the Dubouszki-129 species of rice.

In the highly infected (in some locations) fields the loss of crop was 50–60%.

In the same year similar symptoms were observed on other species as well. The nature of the infection was investigated on these crops and several attempts were made to work out suitable methods for the treatment and prevention of the infection. (Taylor, A. L.: Report About Nematoda Problem of Rice at the Hungarian Rice Production, 1976; Mrs. Simon: Novel Rice Disease: Nematoda Disease of Rice, MÉM Informéciós Központ, No. 156)

The rice leaf nematoda (*Aphelenchoides besseyi Christie*) causes the disease of rice, which spreads (in inactive state) mainly with the seed.

The most suitable manner for controlling this disease is the prevention, i.e. the use of nematoda-free seed, as the spreading of the disease could be inhibited with great difficulty and would cause great expense.

A known method for making nematoda-free seeds is the treatment with warm (52°–53° C.) water, but this method is not suitable for the treatment of seeds of large scale.

Some chemicals were also suggested for this purpose, however, as they are harmful and damage the plant embryo, they are not used in agricultural practice.

It can be stated that there is no suitable method for the prevention of nematoda disease which could be applied on a large scale.

Our aim was to eliminate the drawbacks of the known methods and to work out a process which the seeds, especially rice can simply be disinfected on large scale with good efficiency.

SUMMARY OF THE INVENTIONZ

According to our method the seeds, especially rice is treated with an acidic solution, then a basic powder is applied onto the surface of the seeds in order to neutralize the acid.

DETAILED DESCRIPTION OF THE INVENTION

The present invention is based on the recognition that if a finely dispersed acidic solution is applied onto the surface of the seeds to be treated the acidic solution permeates the glumellas covering the seed, the shell or peel of the seed, etc.

We also discovered that the pests spreading with seeds, e.g. in case of rice, nematodas, bacterias, fungi can be controlled by the above treatment.

According to the present process the disinfection of seeds is carried out by applying a finely dispersed acidic solution onto the surface of seeds, the acidic treatment is continued for a certain time depending on the sensitivity of the pest to be controlled and the species of the seed, thereafter a suitable amount of alkaline power is applied onto the surface of seeds in order to stop the activity of the acid while in order to maintain the uniform dispersion, continously keeping the seeds going.

The treatment is finished when the suitable amount of the alkaline powder is taken up by the seed.

The main advantage of the process of the invention are as follows:

Due to the absorption of the alkaline powder the seed is obtained in dry form, it can be put in sacks, stored or seeded at once without further operation steps.

No harmful chemical is incorporated into the soil with the seed coated according to the process of the invention. Thus the bacteria flora of the soil is not damaged and the pesticidal load of soil is not increased.

The effect of the acidic-basic seed coating is multiple, not only nematodas, but any other pests, bacteria, fungi living in the seed can be controlled.

In the process of the invention mineral acids, e.g. hydrochloric acid, sulfuric acid, sulphonic acid, phosphoric acid, nitric acid or organic acids, e.g. formic acid, acetic acid, lactic acid, tartaric acid, benzenesulphonic acid, etc. can be used. As acid hydrochloric acid is preferable.

The acid usually used in a concentration of 0.5–50 g/l, most conveniently 1–10 g/l.

The acidic solution is used in an amount of 0.01–50 l, preferably 0.05–5 l calculated for 1 kg of seed to be treated.

As alkaline powder e.g. alkaline metal or alkaline earth metal carbonates or -hydrocarbonates, -hydrogenphosphates or -dihydrogenphosphates, etc. can be used. The alkaline metal carbonates are the most preferable.

The alkaline powder is used in an amount of 10–2000 g, preferably 30–100 g calculated for 1 kg of seed.

The seeds are kept in motion during the application of the alkaline powder by stirring or they are placed in an apparatus which is moved, e.g. rotated in the course of the alkaline treatment.

The invention is illustrated by the following, non-limiting examplex.

In order to demonstrate the wide applicability of the method of the invention, the seeds of a mono- and a dicotyledonous plant were coated. The examples were carried out by using pea (*Pisum sativum*) belonging to the class of Dicotyledonospida and rice (*Oryza sativa*) belonging to the class of Monocotyledonopsida.

EXAMPLE 1

1000 g of pea seeds were sprayed with 100 ml of 4% by weight of hydrochloric acid solution, the seeds are stirred for 3 hours, thereafter 45 g of finely powdered magnesium carbonate are dusted to the wet surface of the seeds.

The thus treated pea seeds are dry, suitable for seeding or storage. Their quality is the same as the untreated ones, however, the bacteria infection (*Pseudomonas pisi*) can completely be controlled by the above treatment.

| Treatment | Germination (%) on the 4th day | on the 7th day | Infection with *Pseudomonas pisi* % |
|---|---|---|---|
| Treated | 70 | 75 | 0 |
| Untreated | 72 | 75 | 22.5 |

EXAMPLE 2

1000 g of rice seeds were sprayed with 120 ml of 4% by weight of hydrochloric acid solution under constant stirring. After 4–5 hours the seeds were dusted by 60 g of finely powdered calcium carbonate.

The seeds thus obtained are dry, suitable for seeding or storage, their quality does not decrease even after several months storage.

| Treatment | Germination (%) on the 4th day following the treatment | on the 8th day following the treatment |
|---|---|---|
| Treated | 92 | 94 |
| Untreated | 92 | 92 |

More pests of rice can be controlled by the above treatment. E.g. *Xanthomonas tanslucens pv. oryzae*, *Piricularis oryzae* and *Aphelenchoides bessey*. This latter one is especially dangerous as this nematoda creep under the glumellas and can be controlled only with great difficulty.

According to the present practice the seeds have been treated with warm water in order to eliminate the nematoda infection, therefore the acidic-basic treatment is compared with this method.

| Treatment | Effect of the treatment of rice seeds against the infection of *Aphelenchoides bessey* — Living *Aphelenchoides bessey* calculated for one seed (pieces) |
|---|---|
| Acidic-basic treatment | 0 |
| Warm water treatment | 2.12 |
| Untreated control | 48.33 |

The control of the pests by the above treatment is a qualitative improvement as the spreading of the disease with the seeds can completely be controlled.

We claim:

1. A method for preventing a nematodal, bacterial or fungal infection in rice-sowing seeds and at the same time for improving the germination of seeds which consists essentially of the steps of:
    (a) applying to the surface of the rice-sowing seeds a finely dispersed acidic solution of a mineral acid or an organic acid in a concentration of 0.5 to 50 g/l, employing 0.01 to 50 liters of the acidic solution per kg of the seeds in order to control the nematodal, bacterial or fungal infection;
    (b) neutralizing the acidic solution applied to the seeds in step (a) by applying to the surface of the seeds 10 to 2000 g of an alkaline power per kg of seeds, during which time the seeds are kept in motion; and
    (c) planting the seeds.

2. The method for preventing a nematodal, bacterial or fungal infection defined in claim 1, wherein according to step (a), the mineral acid is used and is selected from the group consisting of hydrochloric acid, sulfuric acid, phosphoric acid, and nitric acid.

3. The method for preventing a nematodal, bacterial of fungal infection defined in claim 1 wherein according to step (a) the organic acid is used and is selected from the group consisting of fumaric acid, acetic acid, lactic acid, tartaric acid, and benzene sulfonic acid.

4. The method for preventing a nematodal, bacterial or fungal infection defined in claim 1 wherein according to step (b) the alkaline powder is selected from the group consisting of alkali metal or alkaline earth metal carbonates, hydrocarbonates, hydrogen phosphates and dihydrogen phosphates.

5. The method for preventing a nematodal, bacterial or fungal infection defined in claim 1 wherein following step (b), the seeds are stored until ready to use.

* * * * *